United States Patent
Xu et al.

(10) Patent No.: US 10,724,897 B2
(45) Date of Patent: Jul. 28, 2020

(54) CASCADED GAPPED CANTILEVER FOR LOW-FREQUENCY VIBRATION SENSING

(71) Applicant: Wayne State University, Detroit, MI (US)

(72) Inventors: Yong Xu, Troy, MI (US); Yating Hu, Detroit, MI (US); Hongen Tu, Detroit, MI (US)

(73) Assignee: National Science Foundation, Alexandria, VA (US)

( * ) Notice: Subject to any disclaimer, the term of this patent is extended or adjusted under 35 U.S.C. 154(b) by 0 days.

(21) Appl. No.: 15/736,046

(22) PCT Filed: Jun. 16, 2016

(86) PCT No.: PCT/US2016/037814
§ 371 (c)(1),
(2) Date: Dec. 13, 2017

(87) PCT Pub. No.: WO2016/205477
PCT Pub. Date: Dec. 22, 2016

(65) Prior Publication Data
US 2018/0172503 A1 Jun. 21, 2018

Related U.S. Application Data

(60) Provisional application No. 62/180,877, filed on Jun. 17, 2015.

(51) Int. Cl.
*G01H 11/08* (2006.01)
*A61B 5/11* (2006.01)
(Continued)

(52) U.S. Cl.
CPC ............ *G01H 11/08* (2013.01); *A61B 5/1102* (2013.01); *A61B 5/4809* (2013.01);
(Continued)

(58) Field of Classification Search
CPC ..... G01H 11/08; A61B 5/1102; A61B 5/4809; A61B 5/6892; G01P 15/09; G01P 15/0922
See application file for complete search history.

(56) References Cited

U.S. PATENT DOCUMENTS 5,563,343 A 10/1996 Shaw et al.
7,360,422 B2 4/2008 Madni et al.
(Continued)

FOREIGN PATENT DOCUMENTS

WO WO-2011119930 A1 * 9/2011 ......... G01C 19/5656

OTHER PUBLICATIONS

Search Report and Written Opinion dated Sep. 7, 2016.

*Primary Examiner* — Peter J Macchiarolo
*Assistant Examiner* — John M Royston
(74) *Attorney, Agent, or Firm* — Fishman Stewart PLLC

(57) ABSTRACT

This disclosure describes a sensor for detecting vibrations, particularly low-frequency vibrations. The sensor is of a cascaded gapped cantilever construction and may include a single sensing beam extending from a base to a proof mass across the plurality of gaps, a mechanical beam opposite the piezoelectric beam. The sensor may be included in a system including a housing, a support, and electronic components for converting and measuring signal. The sensor may be mounted to an item of furniture, such as a bed or a sofa, and measure physiological data including ballistocardiogram and respiratory data of a subject positioned on the furniture.

20 Claims, 7 Drawing Sheets

(51) Int. Cl.
*A61B 5/00* (2006.01)
*G01P 15/09* (2006.01)

(52) U.S. Cl.
CPC ............ *A61B 5/6892* (2013.01); *G01P 15/09* (2013.01); *G01P 15/0922* (2013.01)

(56) References Cited

U.S. PATENT DOCUMENTS

| | | |
|---|---|---|
| 9,048,419 B2 * | 6/2015 | Xu .......................... G01P 15/09 |
| 2008/0265712 A1 | 10/2008 | Ulm et al. |
| 2010/0270889 A1 | 10/2010 | Xu et al. |
| 2013/0204571 A1 | 8/2013 | Savchenko et al. |
| 2014/0183669 A1 | 7/2014 | Xu et al. |
| 2015/0128346 A1 | 5/2015 | Hollyoak et al. |

\* cited by examiner

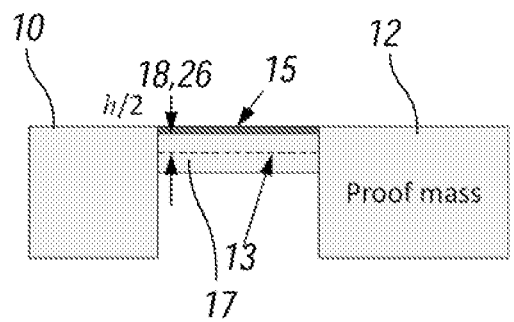
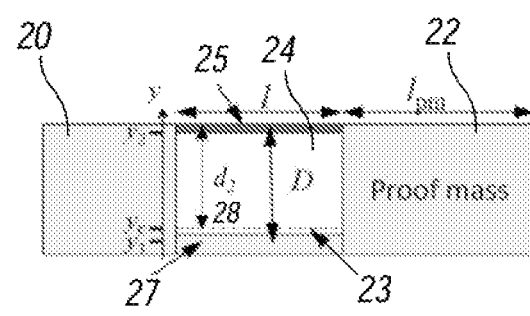
FIG. 1A  FIG. 1B
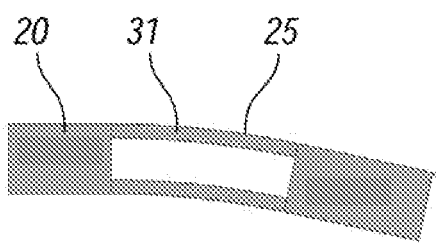
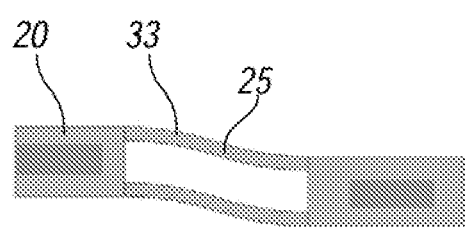
FIG. 2A  FIG. 2B

CASCADED GAPPED CANTILEVER FOR LOW-FREQUENCY VIBRATION SENSING

RELATED APPLICATIONS

This application is a 371 national stage application of PCT/US2016/037814, filed Jun. 16, 2016, entitled "A CASCADED GAPPED CANTILEVER FOR LOW-FREQUENCY VIBRATION SENSING," which claims priority to U.S. Provisional Patent Application Ser. No. 62/180,877, filed Jun. 17, 2015, the entire contents of which are incorporated herein by reference.

FEDERALLY SPONSORED RESEARCH AND DEVELOPMENT

This invention was made with government support under NSF 0747620 and NSF 1030779 awarded by the National Science Foundation. The government has certain rights in the invention.

BACKGROUND

1. Technical Field

The present disclosure relates to sensors for detecting vibrations. More particularly, the present disclosure relates to cantilever structures for use in vibration sensors which incorporate piezoelectric materials.

2. Background Information

In the United States, cardiovascular diseases are the leading cause of death, with treatment costing more than 300 billion dollars annually. Various wearable devices, such as wearable electrocardiogram (ECG) equipment, have been developed for continuous monitoring of cardiovascular parameters in an effort to obtain more complete and timely information of cardiovascular conditions. Nevertheless, wearable devices are not convenient to wear and a large percentage of patients are not willing to wear these devices, even though the devices can improve health and even save the lives of patients using them. This is a significant obstacle for wearable health monitoring, and a major reason that wearable health monitoring is not growing as quickly as expected.

Moreover, low-frequency vibrations, such as those produced by heartbeat and respiration, may prove difficult to detect by sensors that have a high spring constant, and by those that are not physically attached to the subject.

It has been a challenge to develop an improved sensor for detecting physiological vibrations in order to monitor vital signs of a subject, which are not physically tethered to the subject to be monitored.

BRIEF SUMMARY OF THE INVENTION

In one aspect, sensor device to be connected to a support and for detecting vibrations is described. The sensor device includes a base for connecting to the support, a proof mass movable relative to the base, and a mechanical beam connecting the base to the proof mass. The mechanical beam has an inner surface. The sensor device includes a piezo beam having a first end and extending to a second end. The piezo beam includes a sensing material. The first end of the piezo beam is attached to the base and the second end is attached to the proof mass. The sensor device also includes at least one ridge extending from the inner surface to the piezo beam. The at least one ridge forms a plurality of gaps between the piezo beam and the mechanical beam. The mechanical beam and the piezo beam are in opposing relationship relative to the at least one ridge such that the movement of the piezo beam is consistent with movement of the proof mass.

In another aspect, a system for detecting vibrations is described. The system includes a support, a base connected to the support, a proof mass movable relative to the base, and a mechanical beam connecting the base to the proof mass. The mechanical beam has an inner surface. The sensor device includes a piezo beam having a first end and extending to a second end. The piezo beam includes a sensing material. The first end of the piezo beam is attached to the base and the second end is attached to the proof mass. The sensor device also includes at least one ridge extending from the inner surface to the piezo beam. The at least one ridge forms a plurality of gaps between the piezo beam and the mechanical beam. The mechanical beam and the piezo beam are in opposing relationship relative to the at least one ridge such that the movement of the piezo beam is consistent with movement of the proof mass. The system may have a housing generally surrounding the sensor device. The housing may be connected to the support. The system may include a printed circuit board which is in connection with the sensor device.

In another aspect, an item of furniture is provided which can detect vibrations due to the inclusion of a sensor device in accordance with the principles of the present invention. The furniture item may be a bed, a hospital bed, a chair, a couch, or any other item of furniture. The sensor device may be mounted to the underside of the item of furniture, or any other location on the item of furniture.

In another aspect, a method of detecting vibrations is disclosed. The method includes the step of using a sensor device as described herein to detect vibrations.

In another aspect, a method of measuring a physiological output is disclosed. The method includes detecting at least one of heartbeat, pulse, respiration, and motion using a sensor device according to the present disclosure. The physiological output may be a ballistocardiogram. The physiological output may be detected without the subject being in direct contact with the sensor device. The subject may be a human being.

The above aspects will now be described in detail with reference to the drawings submitted herewith.

BRIEF DESCRIPTION OF THE DRAWINGS

FIG. 1A is a schematic side view of a prior art piezoelectric sensor;

FIG. 1B is a schematic side view of a single-gap air space cantilever vibration sensor;

FIG. 2A is a simplified schematic representation of the single-gap cantilever of FIG. 1B undergoing pure bending;

FIG. 2B is a simplified schematic representation of the single-gap cantilever of FIG. 1B undergoing S-shape bending;

DETAILED DESCRIPTION OF THE DRAWINGS AND THE PRESENTLY PREFERRED EMBODIMENTS

Figure 3A:
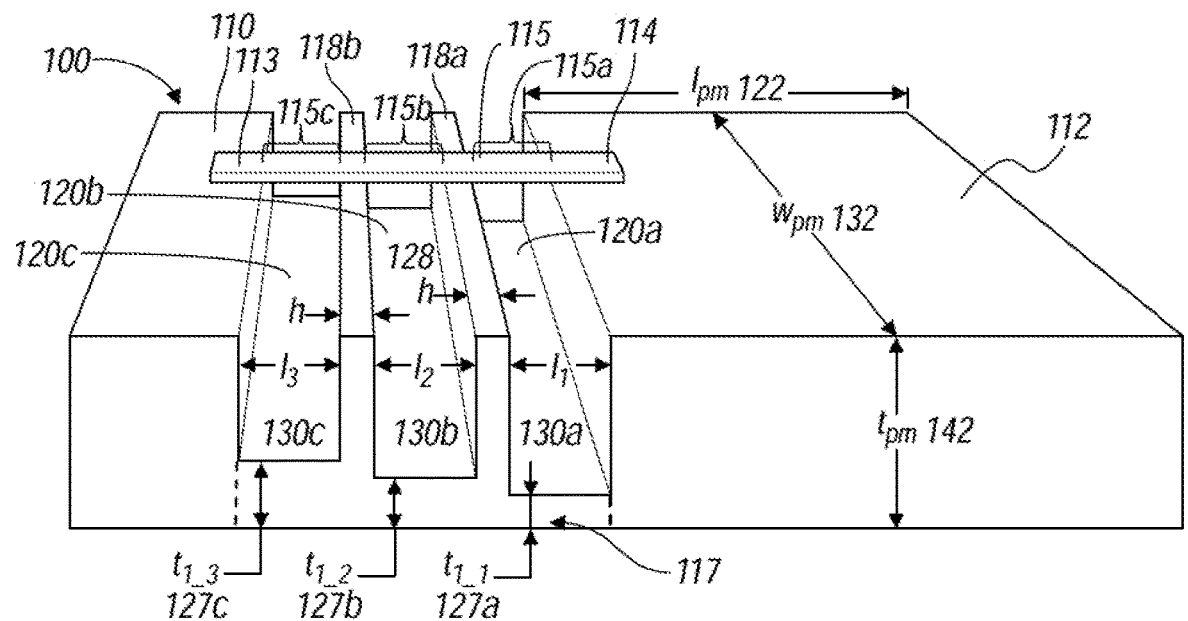
FIG. 3A is a schematic perspective view of a multiple-gap cantilever sensor in accordance with one embodiment of the present disclosure.

As used herein with regard to a range, the term "between" is inclusive of the endpoints of said range, unless it is clear that the endpoints are excluded.

As used herein, the terms "substantially" and "about" mean "approximately but not necessarily exactly," and when used in the context of a numerical value or range set forth means a variation of ±20%, or less, of the numerical value. For example, a value differing by ±20%, ±15%, ±10%, or ±5%, or any value in the range between −20% and +20%, would satisfy the definition of "substantially" or "about."

Vibration sensing using piezo devices has many useful applications. A particularly useful piezo device is described by and encompassed in the claims of U.S. Pat. No. 9,048,419, the entirety of which is hereby incorporated by reference, and which discloses a device having an air space cantilever arrangement, wherein the air space cantilever arrangement includes two first beams and one second beam that are straight and parallel to each other and separated from one another by spaces, the piezo device further comprising a mounted base coupled to a first end of each of the first and second beams and a proof mass coupled to a second end of each of the first and second beams, the second end being opposite the first end, wherein the proof mass is configured to oscillate in an oscillation plane relative to the base upon excitation and to bend the first and second beams during oscillation, wherein the first beams are offset from each other in a direction perpendicular to the oscillation plane. However, for low-frequency vibrations, an improvement can be made by utilizing a new structure, a cascaded gapped cantilever, as described herein.

A cascaded gapped cantilever can be used in a sensor in the generation of a ballistocardiograph. Such a sensor may be used as a heart rate monitor or a sleep monitor. In some instances, the sensor may be attached to or embedded in an article of furniture, such as a bed or a chair, in order to monitor the vital signs of a person occupying the article of furniture.

Described herein is a cascaded gapped cantilever, for low frequency vibration sensing. Previously developed was an asymmetric-gapped cantilever for high-performance vibration sensing. Such a structure is able to increase the sensitivity and improve the energy efficiency significantly. However, improvements for low-frequency sensing are still possible.

FIG. 1A illustrates a conventional cantilever piezoelectric sensor 10 in a schematic view, in contrast to a high performance vibration sensor 20 based on an asymmetric-gapped cantilever in FIG. 1B. The top beams 15/25 are formed by a piezoelectric sensing layer; in the conventional cantilever, this top beam 15 is in contact with the mechanical beam 17, but in the asymmetric-gapped cantilever 20 of FIG. 1B, the piezo beam 25 is separated from the bottom mechanical beam 27 by a gap 24. The piezo beam 15 is in contact with the air of the gap 24. The strain experienced by the sensing layer 15/25 is proportional to the distance 18/28 between the sensing layer 15/25 and the neutral plane 13/23. This distance 28 for the asymmetric-gapped cantilever 20 is $d_2 = y_2 - y_c$, whereas for the conventional cantilever shown in FIG. 1A, it is typically only half of the cantilever thickness $h/2$ (26). Because of the gap 24, $d_2$ can be much larger than $h/2$. Therefore, if the spring constants of the two designs are equal, the sensitivity of the gapped design could be significantly higher than the conventional design.

The deflection of the asymmetric-gapped cantilever 20 under acceleration can be decomposed into pure bending 31 (FIG. 2A) and shear bending 33 (FIG. 2B). Shear bending may undesirable because it leads to opposite stresses along the thickness direction of the piezoelectric layer 25, thus cancelling the voltage or charge generated by its bending.

Figure 3B:
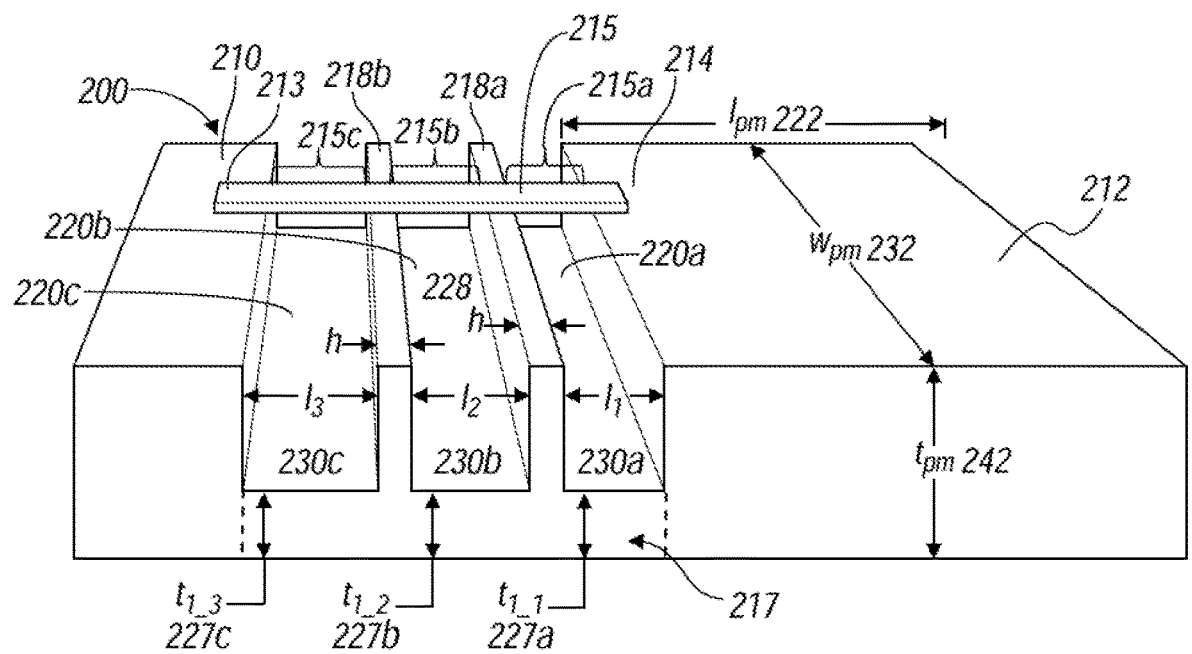
FIG. 3B is a schematic perspective view of a multiple-gap cantilever sensor in accordance with another embodiment of the present disclosure.

Turning now to FIGS. 3A and 3B, two cascading asymmetric-gapped cantilevers 100 and 200 are illustrated. Although these designs are only two of many possible designs contemplated in accordance with the principles of the present disclosure, the portions thereof will serve as illustrations of the concepts described below.

Spring constants for the pure bending $k_P$ and shear bending $k_S$ are described by Equations 1 and 2 respectively:

$$k_P = \frac{4R_P}{l(l + l_{pm})^2} \quad \text{(Equation 1)}$$

$$k_S = \frac{12R_S}{l^3} \quad \text{(Equation 2)}$$

In these equations, l is the cantilever length and $l_{pm}$ is the proof mass length. The bending rigidities for pure bending $R_P$ and shear bending $R_S$ are given by:

$$R_P = E_1(I_1 + A_1 d_1^2) + E_2(I_2 + A_2 d_2^2) \quad \text{(Equation 3)}$$

$$R_S = E_1 I_1 + E_2 I_2 \quad \text{(Equation 4)}$$

In Equations 3 and 4, $A_1$, $A_2$ are cross sectional areas; $E_1$, $E_2$ are Young's moduli, and $I_1$, $I_2$ are moments of inertia of the bottom (mechanical) beam and top (piezo) beam, respectively. $d_1 = y_c - y_1$, $d_2 = y_2 - y_c$ are the distances between bottom/top beams to the neutral plane (see FIG. 1B.)

The average normal strain experienced by the top piezoelectric beam is described by Equation 5:

$$s_2 = \frac{ma(l + l_{pm})}{2R_P} d_2 \quad \text{(Equation 5)}$$

Therefore, the strain sensitivity ($s_2$) is proportional to $d_2$, the distance between the sensing layer and neutral plane. The gapped design therefore has a greater strain sensitivity as compared to a conventional cantilever, which permits greater ability to identify lower-frequency vibrations, such as those caused by physiological processes including heartbeat, pulse, and respiration.

In a gapped cantilever design, shear bending (33, FIG. 2B) should be minimized because it does not effectively generate output signal on the piezoelectric layer. The relation $\eta_1 = k_S/(k_P + k_S)$ represents the percentage of the energy stored in the form of pure bending (31, FIG. 2A). Therefore, as pure bending 31 becomes the dominant form of bending, $\eta_1$ approaches 1. In such a case, $k_S \gg k_P$. Taking the other properties into account, $$\frac{k_P}{k_S} = \frac{1}{3(1 + l_{pm}/l)^2} \frac{R_P}{R_S} \ll 1 \quad \text{(Relation 6)}$$

Since $R_P$ is always greater than $R_S$ as shown in Equations 3 and 4, the only way to satisfy the above requirement is to make $l_{pm} \gg l$. When Equation 6 is satisfied, the effective spring constant of the cantilever is dominated by pure bending. To concentrate the strain energy to the sensing beam in the form of normal strain, the cross sectional areas of the top (piezo) and bottom (mechanical) beams should satisfy Equation 7:

$$\frac{E_2 w_2 t_2}{E_1 w_1 t_1 + E_2 w_2 t_2} = \frac{1}{\sqrt{12}} \frac{t_1}{y_2 - y_1} \quad \text{(Equation 7)}$$

When Equation 7 is satisfied, the effective spring constant can be estimated by Formula 8:

$$k \approx \frac{4 E_2 A_2 d_2^2}{l(l + l_{pm})^2} \quad \text{(Formula 8)}$$

For low-frequency vibration sensing, reduction of spring constant assists in achieving higher sensitivity. Based on Formula 8, one way this can be accomplished is by reducing the cross sectional area of the sensing (piezo) beam $A_2$. However, this will make the manufacturing or fabrication of the sensor challenging and pose reliability issues.

Alternatively, the cantilever length l can be increased. However, this will make the shear deformation of the asymmetric-gapped cantilever dominant and reduce the energy efficiency, since $k_S$ is inversely proportional to $l^3$ as shown in Equation 2.

Figure 3C:
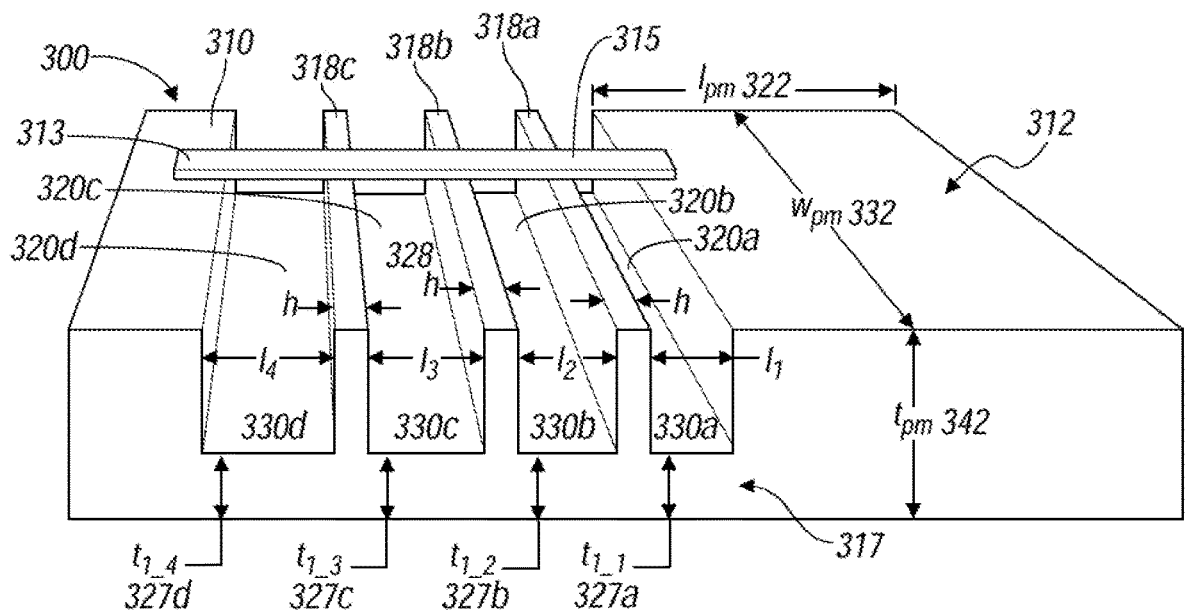
FIG. 3C is a schematic perspective view of a multiple-gap cantilever sensor in accordance with another embodiment of the present disclosure.

Another way to address this issue is by using the cascaded asymmetric gapped cantilever of the present disclosure to lower the spring constant while maintaining the dominance of pure bending. A sensor design based on a three-stage cascaded gapped cantilever is schematically illustrated in FIGS. 3A-3B, and a four-stage cascaded-gapped cantilever is shown in FIG. 3C.

In the embodiment of FIG. 3A, a sensor device 100 is shown having a base 110 connected to a proof mass 112 by a mechanical beam 117. The mechanical beam 117 is the portion of the device which extends from the proof mass 112 to the base 110 and provides its inner surface portions 120a/120b/120c to form the bottoms of gaps 130a/130b/130c. The piezo beam 115 extends from a first end 113 (attached to the base) to a second end 114 which is attached to the proof mass. The piezo beam 115 extends over the gaps 130a/130b/130c. The piezo beam 115 can be attached to the base 110 and the proof mass 112 by any conventional means, such as by using an adhesive, by soldering, by welding, and the like.

The gaps are defined by the ridges 118a/118b. For the plurality of ridges, a gap may be defined between the proof mass 112 and the first of the plurality of ridges 118a, and between the base 110 and the last of the plurality of ridges 118b, and between all other ridges. As illustrated in the embodiment of FIG. 3A, the ridges 118a/118b both have equal widths (128) represented by quantity h. The piezo beam 115 may be in contact with the ridges 118 during bending, or when the device is not bent, or both. The piezo beam 115 may be adhered to the ridges or may be free of them, though able to contact them. In one embodiment, the piezo beam 115 is connected to, or adhered to, all of the ridges 118, and in contact with all of the ridges 118. The piezo beam 115 may be attached to the ridges by an adhesive, such as a glue, or by any other known attachment mechanism, and may be attached such that the piezo beam 115 is in substantially direct contact with the ridges 118. The ridges 118 may extend such that they are substantially perpendicular to the mechanical beam 117, to the piezo beam 115, or in some embodiments, to both.

The base 110 of the device may be secured on any side to a support (not shown). Vibrations are transmitted through the item to which the sensor device 100 is mounted through the base, and the securement allows the proof mass to oscillate relative to the base, and base relative to the proof mass, such that bending of the piezo beam 115 can occur, then providing an electrical signal that can be read, stored, and analyzed. The motion of the proof mass may be as oscillation in a plane substantially perpendicular to the remainder of the device (i.e., an oscillation plane).

The proof mass 112 has a length 122, a width 132, and a thickness 142.

The sensor device 100 may include a body of unitary construction, with the base 110, the mechanical beam 117, and the proof mass 112 being monolithic and formed of a single precursor material, or molded from a starting material into a single body. In some embodiments, the device may be made of a metal, such as copper. In other embodiments, the device may be made of at least one of a plastic, a ceramic, and a polymer. In such a device, it may be advantageous to include a cavity within the proof mass 112 which can then be filled with a relatively heavy material, such as a metal, in order to provide a heavier proof mass. Alternatively, each of the base, the mechanical beam, and the proof mass can be made of a separate part, or may be made of a combination of parts and joined by any known means.

The piezo beam 115 may be a single piezo beam. In some embodiments, the device may include only a single piezo beam. Such a construction provides the advantages of ease of manufacture and reduction of cost. The piezo beam 115 moves consistently with the movement of the proof mass 112 during bending and is made of a sensing material which produces an electrical change in response to mechanical pressure. Particularly suited for this application are piezoelectric and piezoresistive materials. Any piezoelectric or piezoresistive material may be utilized. In particular, lead zirconate titanate (PZT) may be used. In other embodiments, a silicon-containing piezoresistive material may be employed. In one embodiment, the piezo beam has a uniform thickness across its entire length. In another embodiment, the piezo beam has a uniform width (parallel to the plane of the mechanical beam) across its entire length.

In the embodiment of FIG. 3A, the gaps have equal stage lengths, such that $l_1=l_2=l_3$. The gaps 130a/130b/130c have different depths, however, with the thickness 127a ($t_{1\_1}$) of the mechanical beam 117 under the gap 130a closest the proof mass being less than the thickness 127b ($t_{1\_2}$), which is in turn less than the thickness 127c ($t_{1\_3}$) of the third and final gap 130c, which is closest the base 110 (although FIG. 3A is not strictly to scale.) Such an arrangement may allow for each segment 115a/115b/115c of the piezo beam 115 to experience the same amount of strain during bending, increasing robustness of the device 110. This design may be employed where the need for a robust sensor outpaces the need for one having somewhat increased sensitivity.

In a similar way, FIG. 3B illustrates a three-gap sensor device 200 with many of the same features of device 100 of FIG. 3A. However, in this case, gaps 230a/230b/230c have substantially the same depth (that is, the mechanical beam 217 has a thickness under each gap which is substantially the same as any other gap; 227a=227b=227c. In this embodiment, the stage length 220a/220b/220c of each gap 230a/230b/230c increases as the gap occurs further from the proof mass 212. That is, 220a<220b<220c. The substantially invariant thickness of the mechanical beam 217 combined with varying stage lengths allows for a similar result as in device 100; that is, the sensor device realizes an increase in sensitivity due to each portion 215a/215b/215c of the piezo beam having substantially the same energy efficiency during use. The stage of the piezo beam 215c closest the base 210 experiences the greatest strain, with each successive stage 215b/215a experiencing less strain the closer to the proof mass 212 (or the further from the base 210). This provides a device 200 of the construction as shown in FIG. 3B with greater sensitivity, though with somewhat decreased robustness. This design may provide advantages under certain circumstances over a similar device in which the stage lengths of all gaps are equal to one another, wherein robustness is less of a concern and high sensitivity is a priority.

FIG. 3C depicts a sensor design similar to that of FIG. 3B, but as a four-stage sensor device 300. The four gaps 330a/330b/330c/330d have a similar arrangement of varied lengths as in FIG. 3B, with successively increasing stage lengths 327a/327b/327c/327d as distance from the proof mass 312 increases. As described previously, the depths of the gaps 330a/330b/330c/330d may be substantially equal, or may differ from one another.

Although three- and four-stage sensors have been described, a sensor in accordance with the principles of the present disclosure can have a number of stages (or gaps) greater than one. For instance, the sensor device may have two stages, five stages, or more than five stages. A smaller proof mass may make an increased number of stages preferred to increase sensitivity. A need for detection of lower frequency signals may also drive an increase in the number of stages. For the ith stage of such a design, $$k_{P\_i} = \frac{4R_{P\_i}}{l_i\left(\frac{l_i + l_{pm}}{2} + \sum_{j=1}^{i-1} l_j + (i-1)h\right)^2} \quad \text{(Equation 9)}$$

$$k_{s\_i} = \frac{12R_{S\_i}}{l_i^3} \quad \text{(Equation 10)}$$

where h is the ridge thickness, $R_{P\_i}$ and $R_{S\_i}$ are the bending rigidities of ith stage, respectively.

The normal strain experienced by the sensing beam of the ith stage is $$\varepsilon_{2\_i} = \frac{ma\left(\frac{l_i + l_{pm}}{2} + \sum_{j=1}^{i-1} l_j + (i-1)h\right)}{R_{P\_i}} d_{2\_i} \quad \text{(Equation 11)}$$

where $d_{2\_i}$ is the distance between the sensing layer and neutral plane of the ith stage.

For a basic design, all stages have identical dimensions, both in depth and stage length. The cross sections of top and bottom beams and the gap of every single stage is optimized using Equation 7 and the length of every stage is equal.

For more advanced designs, one or more stages may have different dimensions. For example, one optimization criterion is to make every stage have the same energy efficiency. Then $k_P/k_S$ should be equal for all stages. Here, if the cross sectional dimensions of every stage are same, $R_P$ and $R_S$ are same for all stages. The only variable is the stage length $l_i$. Therefore, based on Equations 9 and 10, Equation 12 is as follows:

$$\frac{\left(\frac{l_1 + l_{pm}}{2}\right)^2}{l_1^2} = \quad \text{(Equation 12)}$$

$$\frac{\left(\frac{l_2 + l_{pm}}{2} + l_1 + h\right)^2}{l_2^2} = \frac{\left(\frac{l_3 + l_{pm}}{2} + l_1 + l_2 + 2h\right)^2}{l_3^2} \ldots =$$

$$\frac{\left(\frac{l_n + l_{pm}}{2} + \sum_{1}^{n-1} l_i + (n-1)h\right)^2}{l_n^2}$$

This relationship can be simplified as Equation 13:

$$\frac{l_{pm}}{l_1} = \frac{l_{pm} + 2(l_1 + h)}{l_2} = \frac{l_{pm} + 2(l_1 + l_2 + 2h)}{l_3} = \quad \text{(Equation 13)}$$

$$\ldots = \frac{l_{pm} + 2(l_1 + l_2 + \ldots + l_{n-1} + (n-1)h)}{l_n}$$

The length of ith stage $l_i$ may then be selected based on Equation 13.

In another case, the design may allow for making every stage experience the same strain. Based on Equation 11, the following relationship emerges in Equation 14:

$$\frac{\left(\frac{l_1+l_{pm}}{2}\right)}{R_{P\_1}}d_{2\_1}=$$
$$\frac{\left(\frac{l_2+l_{pm}}{2}+l_1+h\right)}{R_{P\_2}}d_{2\_2}=\frac{\left(\frac{l_3+l_{pm}}{2}+l_1+l_2+2h\right)}{R_{P\_3}}d_{2\_3}=$$
$$\ldots=\frac{ma\left(\frac{l_n+l_{pm}}{2}+\sum_{j=1}^{n-1}l_j+(n-1)h\right)}{R_{P\_n}}d_{2\_n}$$

(Equation 14)

Stage lengths also play a role; if $l_i$ is made equal for all stages, or if they are selected based on Equation 13, $R_{P\_i}$ will be selected based on the above relationship. To lower the fabrication cost, the dimension of the piezo beam 115 typically remains unchanged for all stages and the mechanical beam 117 widths are same as the proof mass 112. The simplest method of choosing $d_{2\_i}/R_{P\_i}$ to satisfy Equation 14 is to vary the thickness of mechanical beam ($t_{1\_i}$) of every stage, as illustrated in FIG. 3A.

In other embodiments, the stage lengths may decrease for each gap in the order from the proof mass to the base.

A sensor device of the present disclosure may be tuned to receive signals optimally at a desired frequency. For example, low frequencies of about 200 hertz to about 220 hertz, and even down to about 50 hertz, have been detected with a device of the present disclosure. A frequency of about 300 hertz, about 500 hertz, about 750 hertz, about 1000 hertz, about 1100 hertz, or higher than about 1100 hertz may be desired for certain applications.

Figure 4:
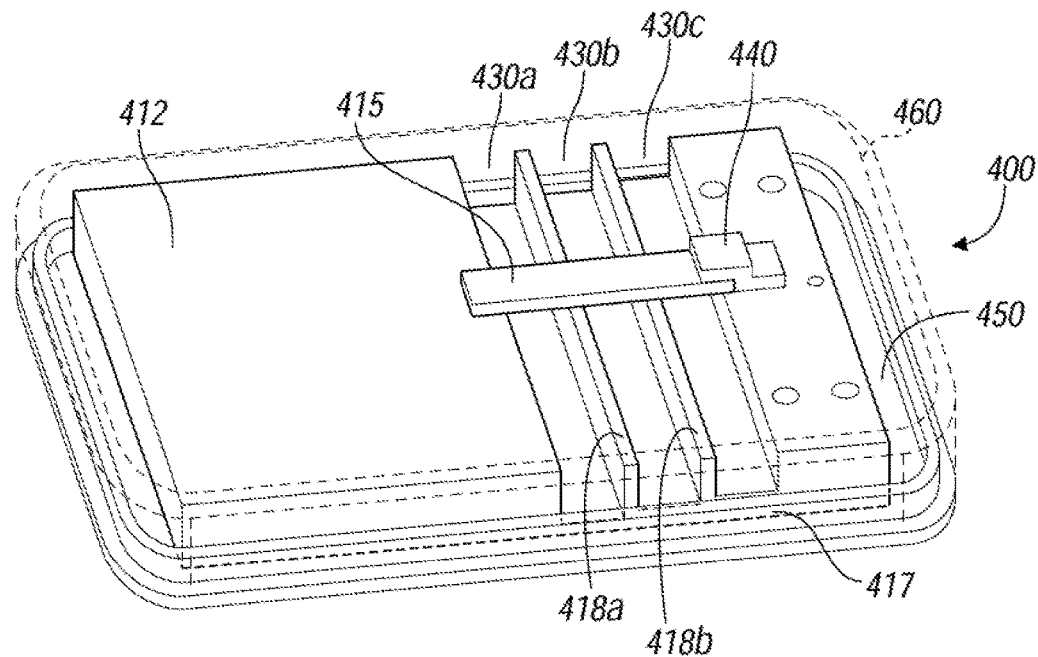
FIG. 4 is a schematic perspective view of a multiple-gap cantilever sensor in a housing, in accordance with another embodiment of the present disclosure.

Turning now to FIG. 4, a vibration sensor 400 is shown generally surrounded by a protective housing 460. The sensor is mounted to support 450, and the housing may extend from support 450 around the device 400 to generally surround it. In one embodiment, the housing 460 is not in contact with the sensor 400 itself, and there is a gap between the sensor 400 and the internal surface of the housing 460. The housing 460 may be made of a plastic, including at least one of an opaque plastic and a clear plastic, among other materials. The sensor 400 is attached by its base 410 to the support 450, such as by screws.

Figure 5:
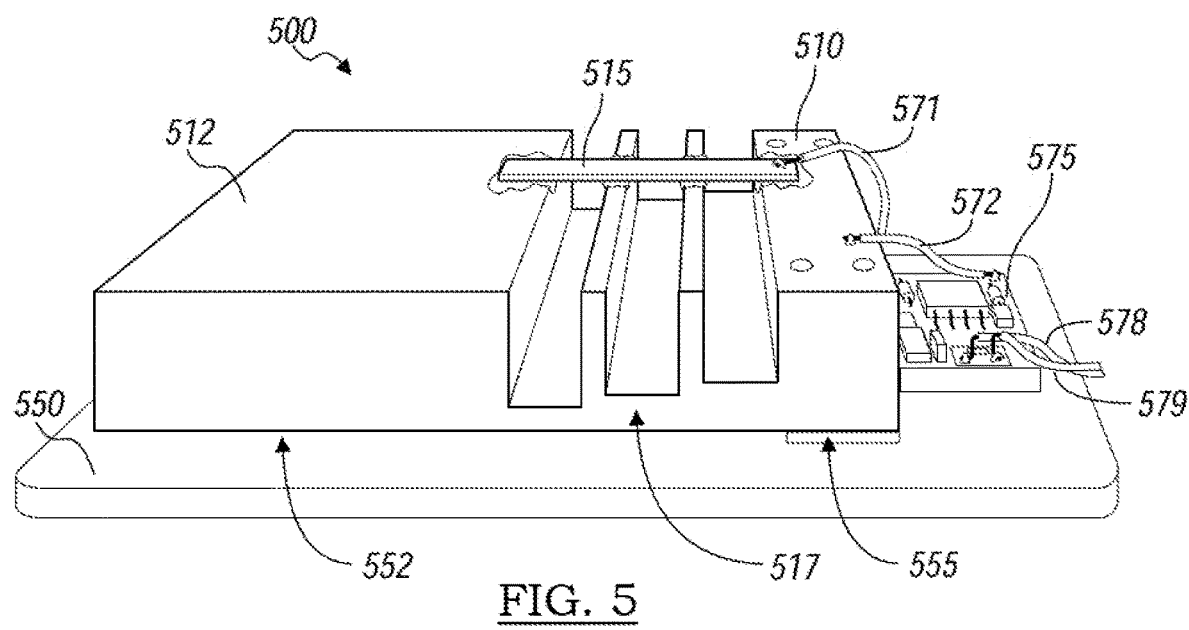
FIG. 5 is a schematic perspective view of a multiple-gap cantilever sensor mounted on a support via a spacer and connected to a printed circuit board, in accordance with another embodiment of the present disclosure.

FIG. 5 illustrates a vibration sensor 500 in the context of a sensor system. The sensor body 500 is precisely machined, such as from a copper piece. In one embodiment, the sensing element or piezo beam 515 may be about 0.5 mm thick PZT. The printed circuit board 575 is in electrical connection with the sensor 500; wire 571 connects the piezo beam 515 to the circuit board 575, and wire 572 connects the base 512 to the circuit board 575. The printed circuit board 575 may include a charge amplifier, and may be in electrical connection to another device (such as a meter, a processor, a monitor, a wireless chip, or a combination of any of the preceding, among others) by wires 578/579. The printed circuit board 575 may also provide a rectifier in order to convert alternating current from bending into direct current. The sensor 500 is anchored to the support 550, such as by using screws. A spacer 555 connects the base 510 to the support 550, forming a gap 552 between the remainder of the sensor 500 (that is, the mechanical beam 517 and the proof mass 512) and the support 550, such that relative motion between the base 510 and the proof mass 512 is facilitated. The system may provide its readout to a battery-powered output, or to one that plugs into a wall source.

The sensor device may be in electrical connection with a reporting mechanism by which a person or computer may view and analyze the data. The data collected may be accessible by internet, by mobile phone, and so forth.

Figure 6:
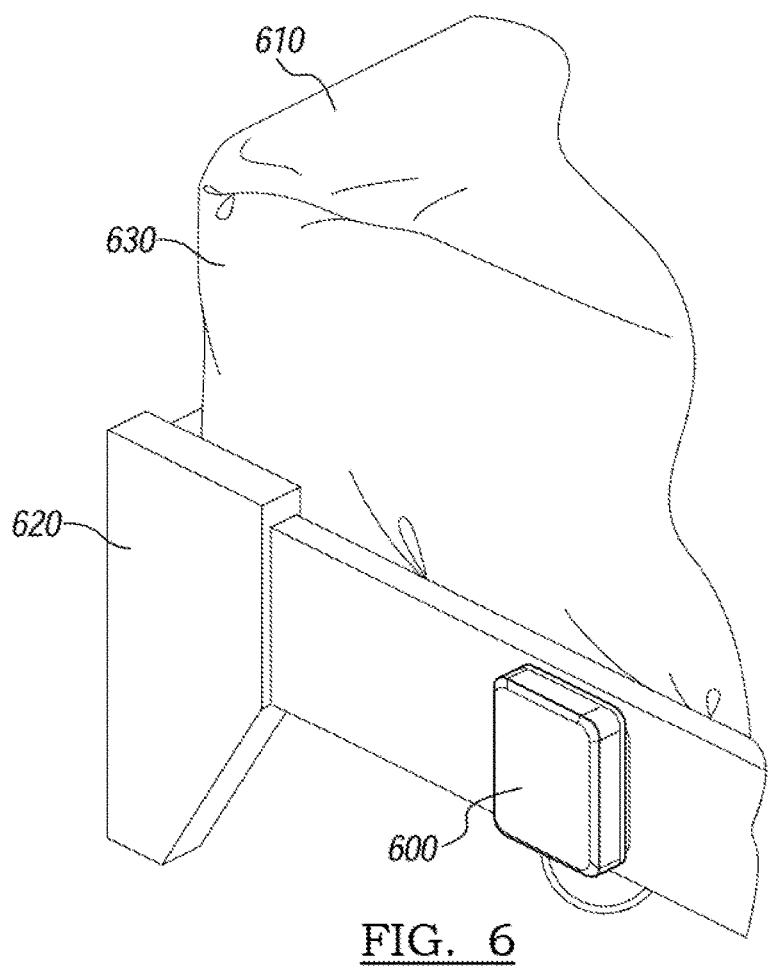
FIG. 6 is a partial perspective view of a vibration sensor mounted to an item of furniture in accordance with another embodiment of the present disclosure.

The sensor according to embodiments of the present disclosure may be useful in numerous contexts. As mentioned, measures of cardiac and respiratory health may represent one way that these low-frequency sensor devices may be used. Because of their high sensitivity, the devices do not need to be in direct contact (i.e., wearable) with the user. FIG. 6 illustrates an example of a sensor device 600 mounted to a bed 610. As illustrated, the sensor device 600 may be mounted to the bed frame 620, but in other embodiments, it may be mounted to a mattress 630, inside of a mattress 630, or to the interior or exterior of a boxspring (not shown.)

A number of physiological readouts have been generated and are interpretable due to signal captured by devices of the asymmetrical, gapped cantilever design of the present disclosure.

Ballistocardiogram (BCG) detection is one application of a device of the present disclosure. BCG is generated by repetitive heart beat and blood ejection forces. The basic information that can be easily extracted from BCG includes heart rate. Therefore, one application of a sensor of the present disclosure is sleep quality monitoring. Compared with other methods, particularly wearables, and such as photoplethysmography (PPG) and electrocardiography (ECG), the sensors of the present disclosure can measure heart rate without direct contact between the subject and the sensor device; that is, no devices or sensors need to be attached to the human body. Therefore, the method of detection is hassle-free and will not cause irritation to the subject.

Figure 7A:
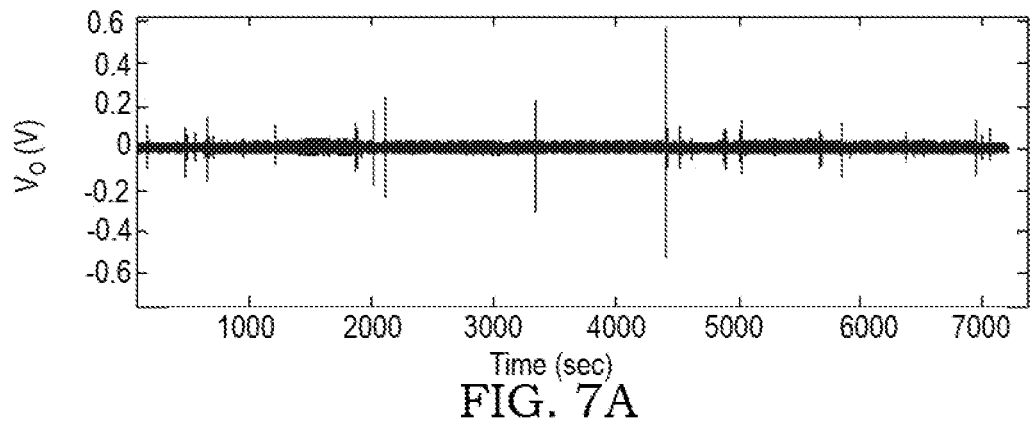
FIG. 7A is a graphical representation of vibration data collected using a device of the present disclosure while a subject was sleeping.
Figure 7B:
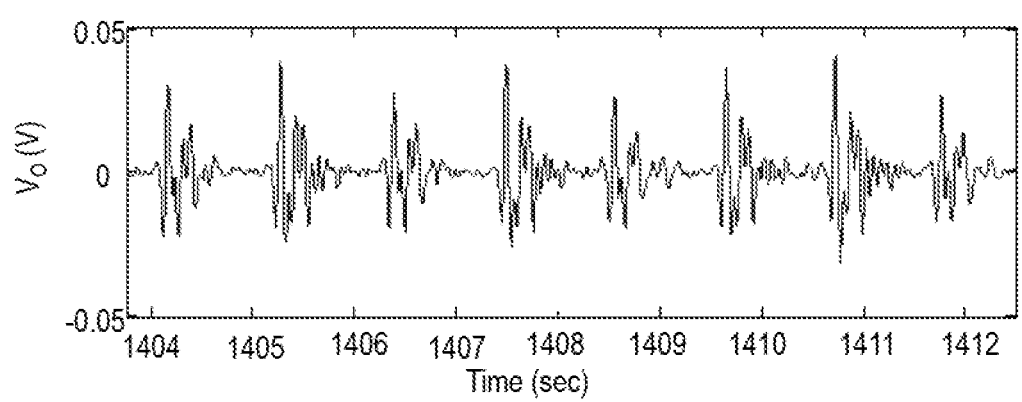
FIG. 7B is an enlarged view of a portion of the graphical representation of FIG. 7A.
Figure 7C:
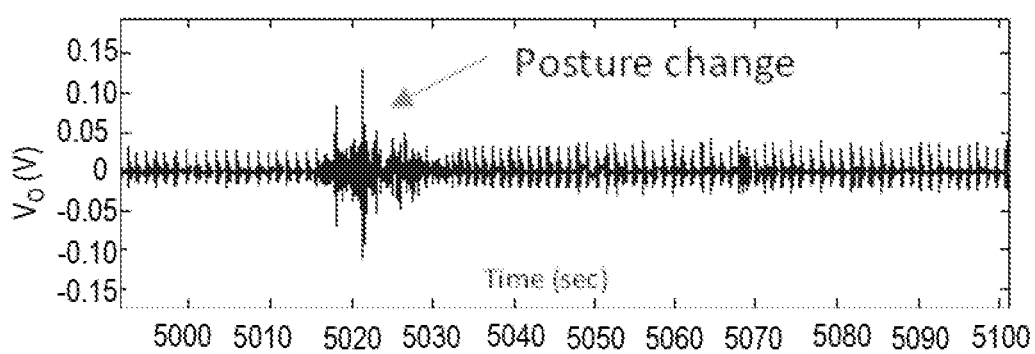
FIG. 7C is an enlarged view of another portion of the graphical representation of FIG. 7A.

FIG. 7A plots a 2-hour period of sleep data. The data were collected by attaching a sensor device of the present disclosure to a bed frame and allowing a subject to sleep in the bed. The large spikes in the BCG are caused by body movements. FIG. 7B focuses on an approximately eight-second window of the two-hour block of FIG. 7A to show the level of detail captured in the BCG signal. FIG. 7C likewise shows an enlarged view of a signal caused by body movement of the subject, together with the BCG pulses. Both BCG signals and body movements such as posture changes are useful information in evaluating sleep quality. In the graphs of FIGS. 7A-7C, the unit of the vertical axis is voltage, and the horizontal axis is time in seconds.

Figure 8A:
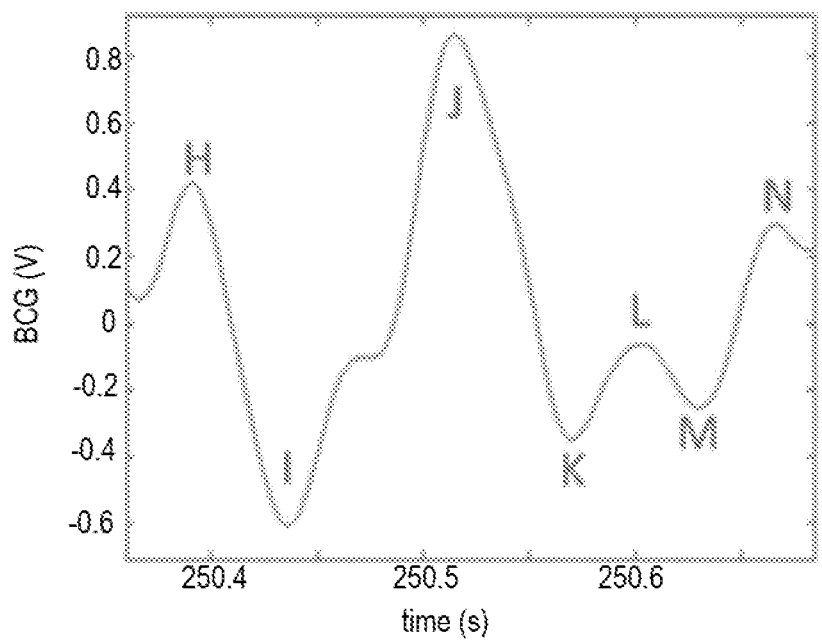
FIG. 8A is a graphical representation of a single ballistocardiogram cycle as recorded by a sensor of the present disclosure.
Figure 8B:
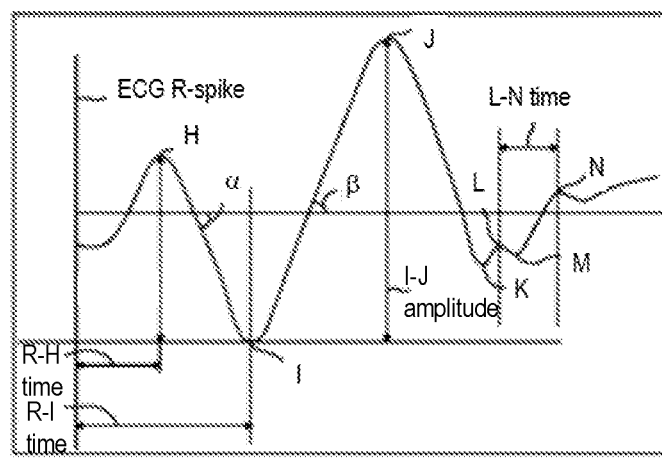
FIG. 8B is a graphical representation of a single theoretical ballistocardiogram waveform for comparison to FIG. 8A.

FIG. 8 illustrates the fidelity between BCG data obtained in the use of a device as described by the principles of the present invention (in FIG. 8A) and the theoretical BCG pattern (FIG. 8B). As can be seen, all features of the BCG are captured by the sensor device of the present disclosure.

Figure 9A:
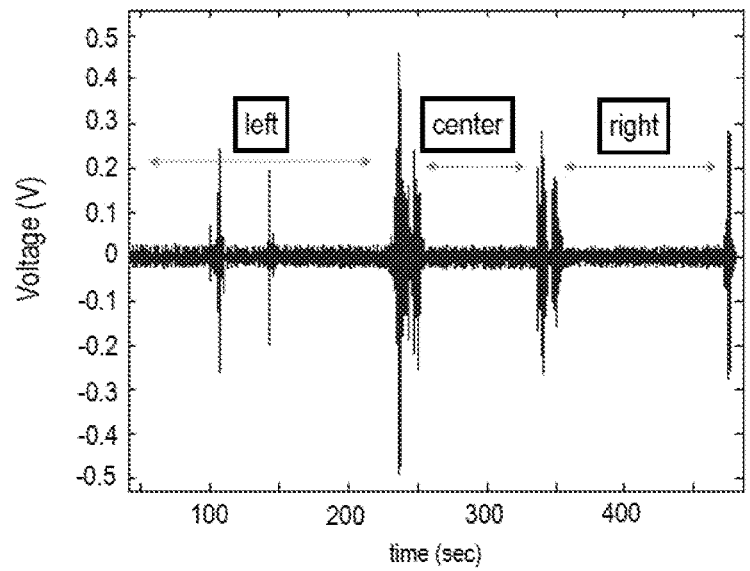
FIG. 9A a graphical representation of vibration data collected using a device of the present disclosure while a subject was sleeping in various locations on a bed.
Figure 9B:
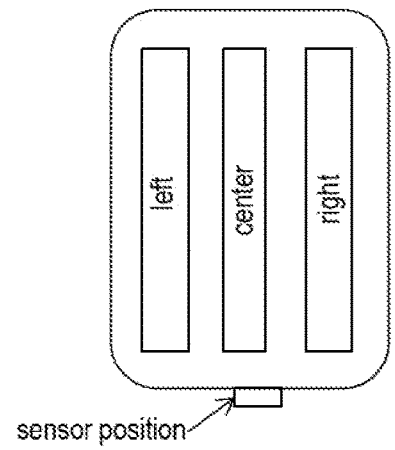
FIG. 9B is a schematic view of positions in the bed according to FIG. 9A.

FIG. 9A-9B demonstrate the convenience of a sensor device of the present disclosure, which has the ability to detect low-frequency signals. In the schematic view of FIG. 9B, the location of a sensor device relative to the location of a subject (center, left, or right of the bed) is seen. The BCG data derived from a person laying in a bed is shown in FIG. 9A. There is substantially no change in magnitude of the BCG data whether the subject is lying in the center, or on one of the sides of the bed. The large spikes are caused by position changes.

Figure 9C:
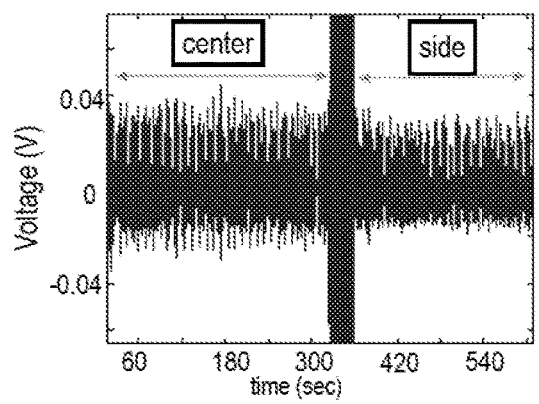
FIG. 9C is a graphical view of vibration data collected using a device of the present disclosure while a subject was sitting in two positions on a sofa to which the sensor was mounted.
Figure 9D:
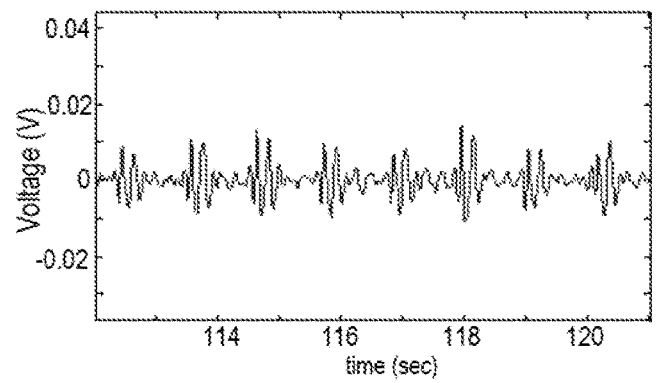
FIG. 9D is an enlarged view of the graphical representation of FIG. 9C.

Other furniture beyond a bed, and indeed other surfaces altogether, can be useful for mounting a device of the present disclosure to acquire physiological data. FIGS. 9C and 9D are BCG data acquired by a sensor device mounted to the center underside of a sofa. A subject sat at the center and at the right side of the sofa and the resultant BCG is shown in FIG. 9C. FIG. 9D provides a detail view of an eight-second window, illustrating that the typical BCG pattern is present. Beyond a sofa, a chair or a hospital bed may also benefit from having a sensor device or system of the present disclosure attached thereto.

Figure 9E:
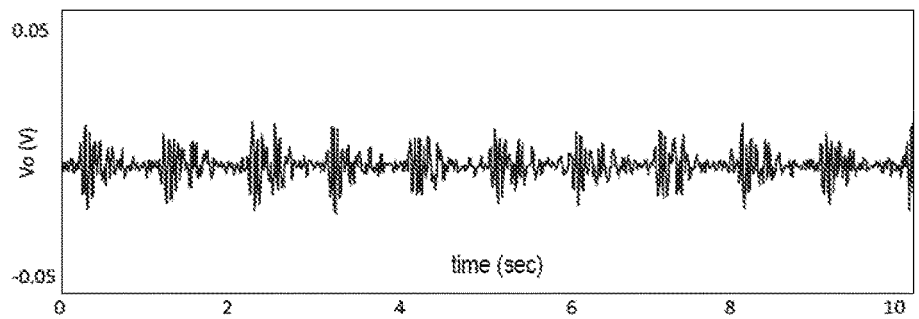
FIG. 9E is a graphical view of a ballistocardiogram collected when a sensor according to the present disclosure was mounted to a floor.

Furthermore, a device of the present disclosure was placed on a carpet-covered floor with a basement underneath, and a subject stood on the floor. The BCG of FIG. 9E is the result of this trial. Despite a small amplitude of this signal, the characteristic BCG trace is clearly discernable. Therefore, 24-hour non-contact monitoring may be achieved by simply mounting a device of the present disclosure to the floor, wall, ceiling, or another surface of the home where the subject resides, or any other space.

Figure 10:
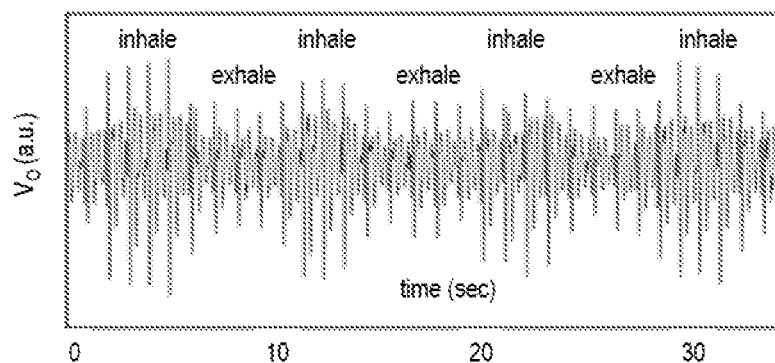
FIG. 10 is a graphical representation of respiratory data extracted from a ballistocardiogram acquired using a device according to the present disclosure.

Finally, in FIG. 10, the impact of respiration on the BCG signal detected by a sensor device of the present disclosure is shown. As can be seen, the amplitude of the BCG signal is modulated by respiration, with increased amplitude during inhalation, and decreased in exhalation. Therefore, respiration information such as rate and magnitude can be derived from BCG. Because dyspnea and apnea are significant symptoms related to heart failure, use of a sensor device of the present construction which is able to collect such data without direct contact with the subject can be a preferred method of monitoring a patient.

In another aspect, a method of monitoring sleep quality is provided. The method comprises the steps of providing a cascaded (multi-gap) asymmetric cantilever vibration sensor, as described herein, and attaching it to a surface. The surface may be a portion of an item of furniture, such as a bed in which the subject is to sleep. The sensor is attached fixedly to the furniture, directly or indirectly, with the proof mass being unfixed. The sensor device is in electrical connection with a device that can store or report the vibration data collected. A health care practitioner, or software, can interpret the vibration data to determine the sleep quality.

Beyond the field of health care and physiology, a sensor device of the present application may find a use in a field that also uses vibrational data, including but not limited to energy harvesting, accelerometers, petroleum-detection and harvesting applications, and earthquake sensing.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

The invention claimed is:

1. A sensor device to be connected to a support and for detecting vibrations, the sensor device comprising:
 a base for connecting to the support;
 a proof mass movable relative to the base;
 a mechanical beam connecting the base to the proof mass, the mechanical beam comprising an inner surface;
 a piezo beam having a first end and extending to a second end, the piezo beam comprising a sensing material, the first end being directly attached to the base, the second end being directly attached to the proof mass; and
 at least one ridge extending from the inner surface of the mechanical beam to the piezo beam, such that the at least one ridge is in direct contact with the piezo beam and forms a plurality of gaps between the piezo beam and the mechanical beam, the mechanical beam and the piezo beam being in opposing relationship relative to the at least one ridge such that the movement of the piezo beam is consistent with movement of the proof mass.

2. The sensor device of claim 1 comprising a plurality of ridges.

3. The sensor device of claim 2, wherein the plurality of ridges are spaced at substantially equal distances from one another, such that each of the plurality of gaps has substantially the same stage length.

4. The sensor device of claim 2, wherein each of the plurality of gaps has a different stage length.

5. The sensor device of claim 4, wherein the stage length of the gap closest the proof mass is less than the stage length of the gap closest the base.

6. The sensor device of claim 4, wherein the stage length of each gap decreases in a direction from the base to the proof mass.

7. The sensor device of claim 4, wherein the stage length of each gap in a device having n gaps in which each of the plurality of ridges have substantially the same width, is defined by the equation:

$$\frac{l_{pm}}{l_1} = \frac{l_{pm} + 2(l_1 + h)}{l_2} = \frac{l_{pm} + 2(l_1 + l_2 + 2h)}{l_3} = \ldots = \frac{l_{pm} + 2(l_1 + l_2 + \ldots + l_{n-1} + (n-1)h)}{l_n}$$

wherein $l_{pm}$ is the length of the proof mass, $l_1$ is the stage length of the gap closest the proof mass, $l_n$ is the stage length of the gap closest the base, and h is the width of the ridges.

8. The sensor device of claim 2, wherein each ridge has substantially the same width.

9. The sensor device of claim 1, wherein the mechanical beam is of uniform thickness adjacent each gap.

10. The sensor device of claim 1, wherein the mechanical beam has a different thickness adjacent each gap, the thickness of the mechanical beam increasing adjacent each gap from the proof mass to the base.

11. The sensor device of claim 1, wherein the sensing material comprises lead zirconate titanate.

12. The sensor device of claim 1, wherein the sensing material comprises silicon.

13. The sensor device of claim 1, wherein the base, the proof mass, and the mechanical beam are of monolithic construction.

14. The sensor device of claim 1, wherein the piezo beam is adhered to each of the plurality of ridges.

15. A system for sensing vibrations comprising:
 a support;
 a sensor device having a gapped cantilever arrangement, the sensor device comprising:
  a base connected to the support;
  a proof mass movable relative to the base and spaced apart from the support;
  a mechanical beam connecting the base to the proof mass, the mechanical beam comprising an inner surface;
  a piezo beam having a first end and extending to a second end, the piezo beam comprising a piezoelectric material, the first end being directly attached to the base, the second end being directly attached to the proof mass; and at least one ridge extending from the inner surface of the mechanical beam to the piezo beam, such that the at least one ridge is in direct contact with the piezo beam and forms a plurality of gaps between the piezo beam and the mechanical beam, the mechanical beam and the piezo beam being in opposing relationship relative to the at least one ridge such that the movement of the piezo beam is consistent with movement of the proof mass; and a housing connected to the support and generally surrounding the sensor device.

16. The system of claim 15, wherein the sensor device comprises a plurality of ridges.

17. The system of claim 15, wherein the housing comprises a plastic layer.

18. The system of claim 15, further comprising a printed circuit board attached to the support and in electrical connection with the sensor device.

19. An item of furniture comprising the system of claim 18.

20. The item of furniture of claim 18, wherein the item of furniture comprises a bed, and the system is mounted to one of a box spring, a frame, and a mattress of the bed.

* * * * *